United States Patent [19]

Gomberoff

[11] Patent Number: Plant 7,643

[45] Date of Patent: Sep. 3, 1991

[54] PEPINO PLANT, CASCADE GOLD

[76] Inventor: Ismael Gomberoff, P.O. Box 262, Lynden, Wash. 98264

[21] Appl. No.: 431,626

[22] Filed: Nov. 3, 1989

[51] Int. Cl.[5] ..... A01H 5/00

[52] U.S. Cl. ..... Plt./89

[58] Field of Search ..... Plt./89

[56] References Cited

PUBLICATIONS

Bailey, L. H., "10. *Muricatum*" *The Standard Cyclopedia of Horticulture,* 1935, The MacMillan Co., N.Y., p. 3182.

ANON, "Pepino—*Solanum muricatum*" *Bulletin* 37, Cornell Univ., Ag. Exp. Sta., Dec., 1891, Cornell Univ., Ithaca, N.Y., pp. 389-394.

Morley-Bunker, M. J. S., "A New Commercial Crop, the Pepino (*Solanum muricatum* AIT) and Suggestions for Further Development", *Annual J. Royal New Zealand Inst. of Hort.,* No. 11, 1983, pp. 8-19.

Redgwell, R. J. et al., (1986), "Pepino (*Solanum muricatum*): Chemical Composition of Ripe Fruit", *J. Sci. Food Agric.,* vol. 37, pp. 1217-1222.

El-Zeftawvi, B. M. et al. (1988), "Some Maturity Indices for Tamarillo and Pepino Fruits", *Journal of Horticultural Sciences,* vol. 63, No. 1, pp. 163-169.

Heiser, C. B., "Pepinos" *Nightshades* (Pub: W. H. Freeman and Co., San Francisco), 1974, pp. 123-127.

Dennis, D. J. et al. (1985), "Pepinos Cultural Techniques an Introduction", *Horticultural Produce & Practice,* Information Services, MAF, Wellington, N.Z., pp. 133-135, 153.

Bravo, A. et al. (1983), *El Campesino,* pp. 16-33 (published in Chile, S.A).

*Primary Examiner*—James R. Feyrer

*Attorney, Agent, or Firm*—George M. Cole

[57] ABSTRACT

The invention relates to a new and distinct variety of *Solanum muricatum* which has been designated the "Cascade Gold" pepino. The subject variety was genetically mutated from plants which originated in La Serena, Chile. This fruit resembles other varieties of pepinos, but is superior to them in respect to having a very sweet flavor with no typical pepino aftertaste, and its ability to set and bear fruit in abundance in Lynden, Wash.

2 Drawing Sheets

BACKGROUND OF THE NEW VARIETY

The present invention relates to a new and distinct variety of pepino plant which has been denominated by the varietal name, "Cascade Gold", and which is characterized as to novelty by producing a fruit of substantial sweetness, lacking the typical "Cucumber" aftertaste, and the stability of the plant to set and bear fruit in the area of Lynden, Wash.

The color of the fruit varies widely from a light green when immature to a yellow-green or yellow in maturity and exhibits a highly variable anthocyanin marking of fruit. These splashes of violet-purple markings can differ greatly from fruit to fruit, and plant to plant. Fruit coloration can range from an almost solid purple with no definite pattern, to an almost solid yellow with little purple, or just a light pin-striping. Coloration is not different from that of the species, nor is it particularly distinguishing. The skin is completely smooth with no rough edges and has a belly button stem area. Skin thickness is also reflective of the species as a whole. The flesh is yellow-orange and has the same basic texture as a musk melon, with a definite cantalope like flavor. This is in deferance to the flavor of the New Zealand pepinos which the Ministry of Agriculture and Fisheries describes as "resembling a musk melon", a fact also born out by actual taste tests with fruit from New Zealand and Chile. The fruit is also quite aromatic when ripe, and has many viable seeds. The flesh coloration and seed production distinguish the new variety from that as described by L. H. Bailey as being "flesh yellow and seedless under cult." There does not seem to be a significant difference in these factors when compared to the current commercial fruit from New Zealand, however.

Outdoors, the plant starts blooming in early June, and starts setting fruit around the 20th of June. It appears that it is irrelevant how large the plant is when placed in the field, as long as it is planted in the ground by May 1. They will begin flowering as stated. This is only true, however, if local weather remains basically within its norms. The mature fruits are harvestable in mid-September thru to the first killing frost. The fruit requires from ninety (90) to one-hundred and ten (110) days to mature.

For eleven years, the applicant has endeavored to produce a new and novel variety of fruit for his enterprise, in Lynden, Wash. In this undertaking, the applicant has through diligence, and trial and error, produced a new variety of pepino.

In 1979, twenty-four seeds from La Serena, Chile were planted in the greenhouse. Half of the seedlings were planted outside, and the rest were grown in the greenhouse. In both areas, the plants did well and produced flowers, but no fruit. Cuttings were taken from the three plants which produced the best overall characteristics of healthy growth and abundant flowers. This process of selective asexual reproduction was continued until 1987, when in mid-August the first fruit was found to have set. In total, twelve fruit were produced on secondary growth of the same primary branch, but none were able to mature fully.

Asexual Reproduction of the New Variety

In May of 1988, eight hundred (800) cuttings made from the plant which produced the fruit were planted. These plants were started from slips in January and grown indoors until planting time. The plants were approximately twelve (12) to eighteen (18) inches in diameter when planted outdoors in cloches, which were removed in early June. Only the one hundred and fifty (150) plants which were started from the specific fruited primary branch produced fruit in any abundance. The fruit set began around June 29, and continued until the first killing frost in mid-October.

This material, which has been denoted as "Cascade Gold", produced from twelve (12) to twenty (20) mature fruit which ranged from three to twenty-one ounces, and averaged over eight ounces each. Also, there were at least as many fruit left on the plants when the first killing frost came, as were harvested.

It was at this time that the applicant discovered that the new fruit had a very sweet flavor and no unpleasant aftertaste which had been experienced when taste testing pepinos from Chile and New Zealand.

The plants derived from the non-producing stems of the original plant produced only sporadic fruit, indicating that a definite genetic mutation had occurred in the specific primary branch which borne the original fruit. Further proof of this change is born out by the fact that as of Aug. 15, 1989, the plants had set fruit in great abundance with from 10 to 40 fruit developing on each plant. And, by November of 1989, a total of eight thousand (8,000) pounds of fruit were harvested, and at least as much was lost in the field to frost. There were numerous plants which had over fifty (50+) fruits each.

In the greenhouse area, there were plants with eighty (80) fruit. In contrast to the Cascade Gold plant, about one-hundred (100) plants were grown from seeds extracted the year before. Of these, roughly 10% of the plants set any fruit at all. And only two or three plants set from ten (10) to fifteen (15) fruits. None of the fruits which were produced by the seed plants were of a commercial value. All had reverted back to the normal pepino flavor with a strong astringent aftertaste.

In 1990, an extremely wet spring and an extremely hot summer delayed the setting of fruit outside until early September, at which time the plants began setting fruit in abundance, but too late for the fruit to mature. Indoors, however, the plants began setting fruit in April and a harvest began in July. The plant has shown to be very stable for setting and bearing fruit when kept between 50 deg. F. and 85 deg. F. It will ripen fruit at higher temperatures but will not set fruit. It is also showing a greater propensity for setting multiple fruit on a single flower truss, that it did the year before. In 1989, two or three fruits on a single truss was the norm for trusses with multiple set fruit. In 1990, there were trusses which contained up to seven fruit. The plant will generally allow only four or five on a truss to grow to a commercial size, however.

BRIEF DESCRIPTION OF THE DRAWINGS

The accompanying drawings show typical specimens of the new variety in color as nearly true as is reasonably possible to make the same in a color illustration of this character. In each instance the photographs were made at Artistic Farms in Lynden, Wash.

DETAILED DESCRIPTION

Figure 1:
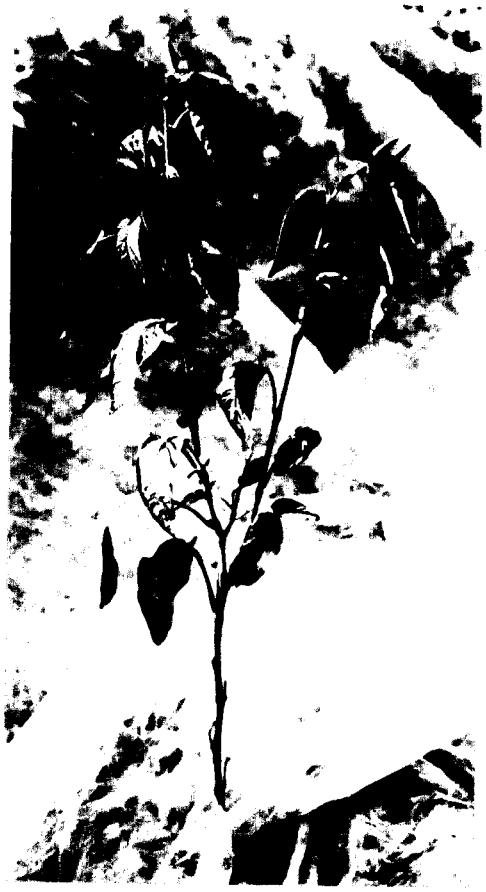
FIG. 1 is a young shoot tip of pepino photographed in August 1989.
Figure 2:
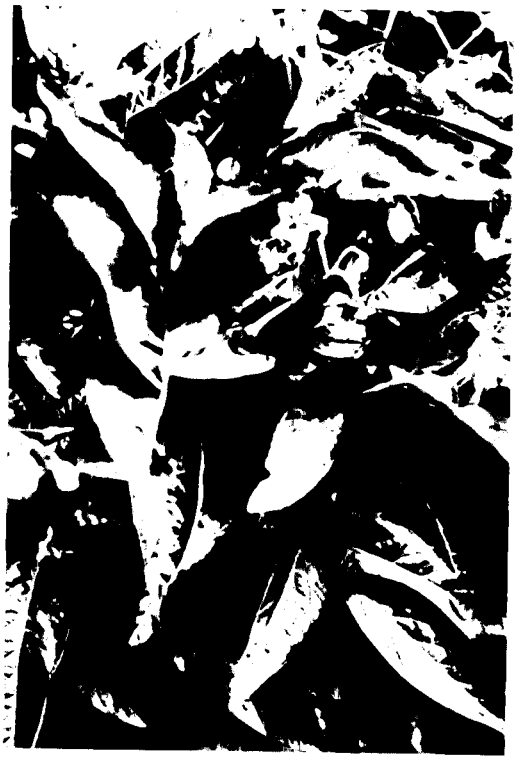
FIG. 2 is a flowering lateral of pepino photographed in August 1989 also showing 2-3 day old set fruit.
Figure 3:
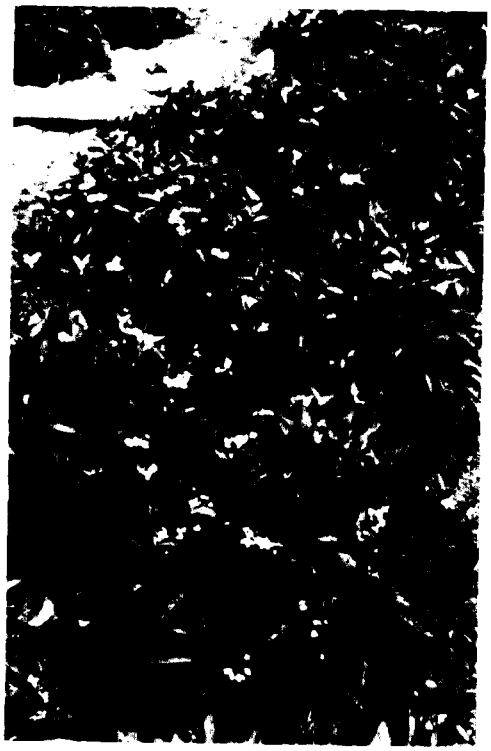
FIG. 3 is a row of pepino planted in May and photographed in July of 1989.
Figure 4:
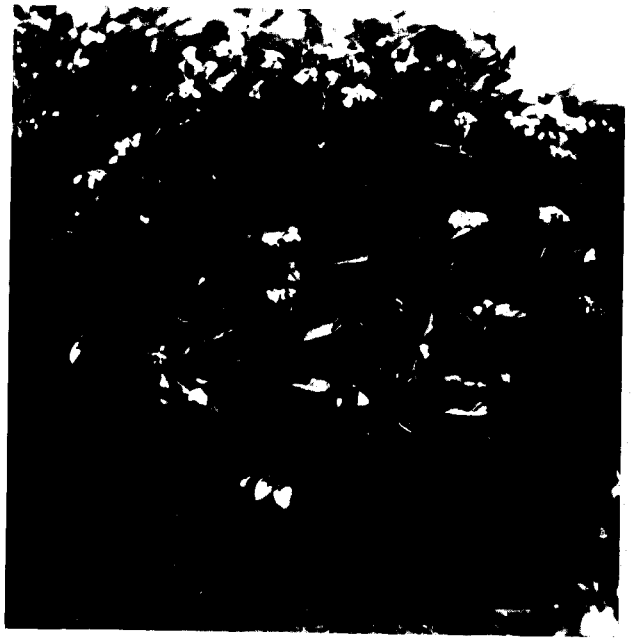
FIG. 4 is a closer view of the row of FIG. 3, photographed in August 1989.
Figure 6:
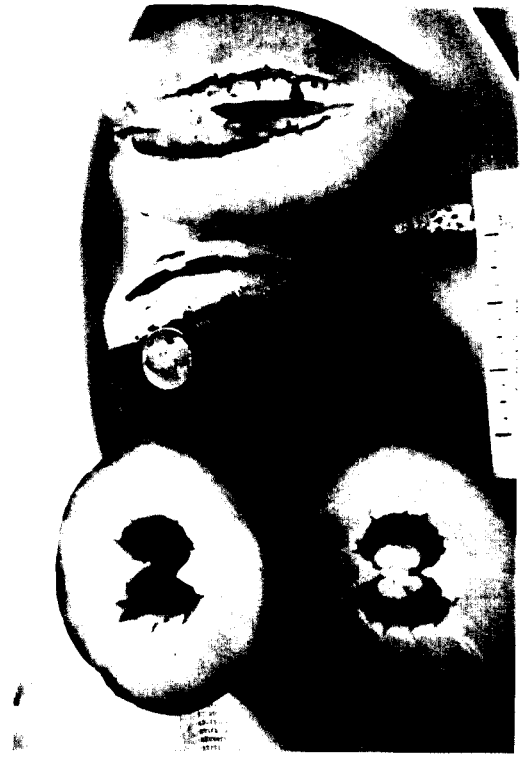
FIG. 6 is a cross section of the fruit cut along the axis, and a fruit split normal to the axis and through the locules to show seed placement.
Figure 8:
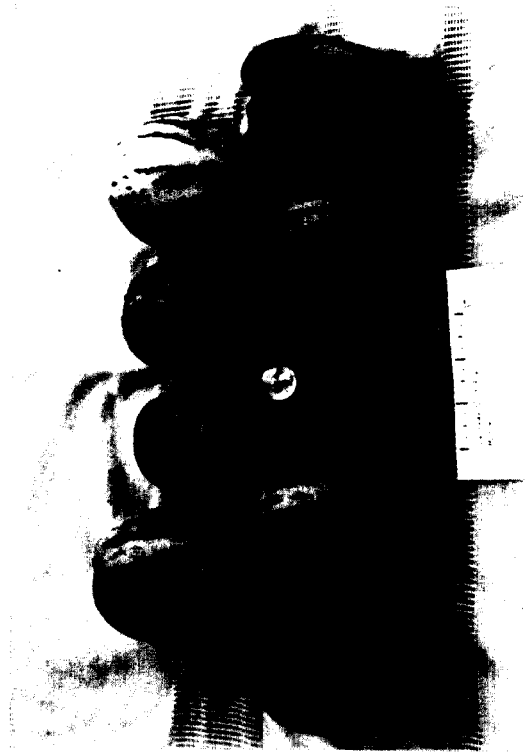
FIG. 8 is a group of pepinos showing the variability of anthocyanin markings and the general heart shape ovoid appearance of the new "Cascade Gold" variety.
Figure 5:
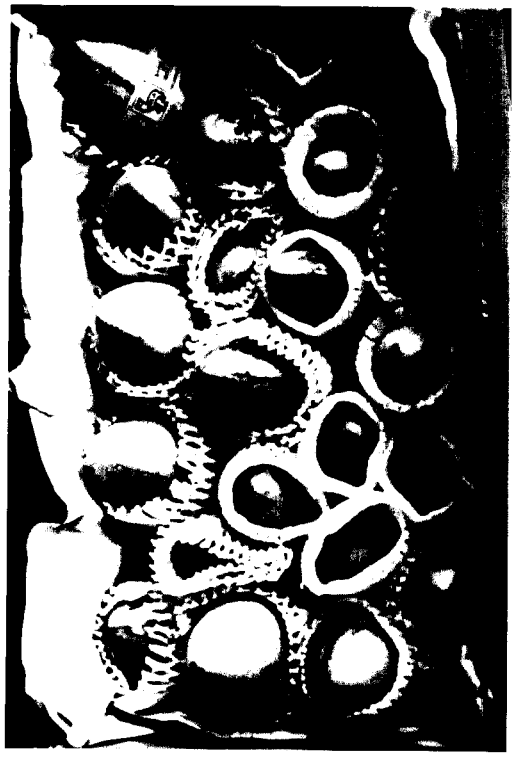
FIG. 5 is a ten pound case of pepinos photographed in August of 1989 and basically fully ripened.
Figure 7:
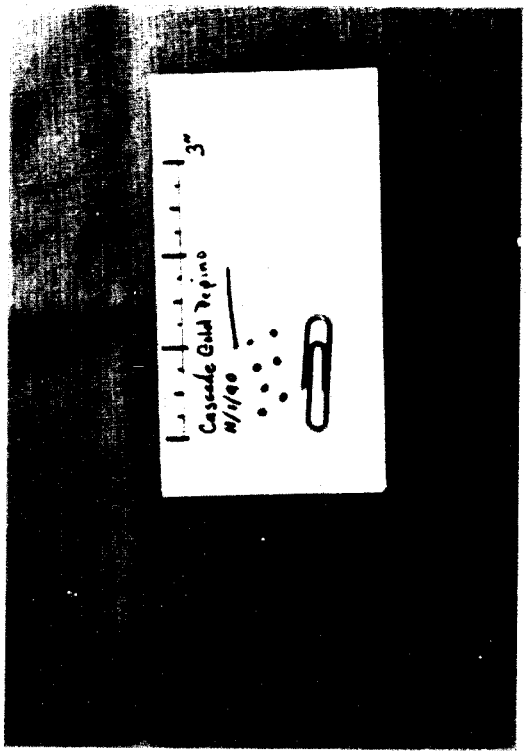
FIG. 7 is a group of seeds showing reniform characteristics and relative size. The seed just below the pin head in on edge to show relative thickness of the seed.

The following is a detailed description of the new variety's characteristics as observed at Artistic Farms. Color terminology employed is to be accorded its ordinary dictionary significance. As will be apparent to those skilled in horticultural science, the color of the fruit varies with the stage of ripeness.

Description of Vegetative Shoots

Herbaceous annual, ca. 4–6 dm tall, branching extensively from the base and along the stems; lower branches developing nodules from which adventitious roots are produced. Stems with swollen nodes and small ridges extending downward from the base of the leaf petiole, generally hispidulose. Leaves alternate, exstipulate, dark, glabrous and shiny green above, paler and lightly to densely pubescent (villous) beneath, especially along the conspicuous veins, becoming glabrate with age. Leaf blades broadly lanceolate, up to 20 cm. in length and 8 cm. in width, entire or occasionally with one or two smaller basal lobes, rounded or cordate at the base; petioles up to 5 cm. long.

General Habit

Strength of growth: Vigorous, sturdy branches produced in high numbers.

Habit of growth: Semi erect in young plants but later spreading as lower branches develop adventitious roots from nodules.

Coloring: Medium green, with splashes of purple in older shoots.

Hairiness: Lightly to densely pubescent on leaves, especially on the underside.

Bloom: Very strong with numerous flowers.

Leaflets: Blades are broadly lanceolate, entire or occasionally with one or two smaller basal lobes.

Leaf:

*Color.*—Dark shiny green above and paler below.

*Petioles.*—Up to 5 cm. in length.

*Veins.*—Conspicuous.

Description of Flowers and Fruit

This variety of pepino is self compatible and readily pollinates itself under field conditions, producing numerous fruits per plant. The fruit is typically light green with whitish specks when immature, turning to yellow-green to yellow covered with splashes of purple when mature. The fruit is very sweet and lacks the typical "soapy" pepino aftertaste. It is ovoid or heart shaped, longstalked, drooping, generally 4 to 6 inches long, and the flesh is yellow-orange, aromatic, tender, and juicy. There are numerous seeds on intruding placentae in the center cavity which is 2-loculed with axile placentation, with the septum disintegrating somewhat at maturity.

The seeds are amphitropous, about 1.5 mm by 2 mm, flattened and more or less reniform. There is no visible difference in the seeds of the new variety as compared to those observed from Chile or New Zealand. The flowers are in a longstalked cluster, rather small, with a pale lavender corolla. They are deeply 5-lobed, and generally are inclined or nodding. When ripe, the fruit separates from the stem much the same way as a ripe strawberry "pops" off. Ripening commences in early September and extends thru the first killing frost.

General Description

Flowers: Few to numerous in corymbose or racemose, extra-axillary inflorescences, more or less nodding.

Pedicel: 8 to 12 mm.

Calyx: Rotate and deeply cleft.

Lobes: Lanceolate, 5 dark purple lobes 5 to 7 mm, densely pubescent (sericeous).

Corolla: Fused at the base, rotate and saucer-shaped, not becoming reflex.

Corolla lobes (petals): Pale lavender, with broad papery-white, wavy margins and a greenish base.

Anthers: Connivent around the style, bright yellow, with terminal pores.

Filaments: Epipetalous, much shorter than the anthers.

Ovary: Superior, two carpellate and two locular (occasionally apparently four locular), with axile placentation.

Seeds: Numerous on intruding placentae, anatropous or somewhat amphitropous ca. 1.5 mm by 2 mm, flattened and more of less reniform.

Fruit: Broadly ovate, 6 to 10 cm. long and nearly as wide, glabrous and shiny, mottled when mature (purple over a yellow to yellow-green background) rather resembling a cucurbit. The fruit weight ranges from approximately 100 grams to 600 grams. There are from one to six fruit per fruited lateral. The fruit has a cantaloupe like flavor and is very juicy with a yellow to yellow-orange flesh.

Quality.—Firm and succulent, very aromatic and sweet.

Season of ripening: Early September through the first killing frost.

Yield: From 4 to 18 kg. per plant.

Disease resistance: The plants are very hardy and show little stress due to late blight or fusarian wilt.

Pests: Aphids, spider mites, green looper catapillars, army worms and poroporo stemborer moth must be monitored closely.

Storage capability: The fruit has excellent storage capabilities and will keep for over a month at 45 deg. F., with little deterioration in fruit quality.

Productivity: Good, dependant on temperatures within norms.

Although the new variety of pepino possesses the desired characteristics under the growing conditions prevailing in Lynden, Wash., in the Nooksack Valley, it is to be understood that variations of the usual magnitude in characteristics incident to changes in growing conditions, fertilization, cultural practices, and pest control are to be expected.

I claim:

1. A new and distinct variety of *Solanum muricatum* (pepino) substantially as illustrated and described, broadly characterized as to novelty by its ability to set abundant amounts of fruits which begin ripening in early September under the ecological conditions prevailing at Lynden, Wash., and by its producing a fruit which is very sweet and lacks the typical astringent aftertaste of its species.

* * * * *